(12) United States Patent
Tadenuma et al.

(10) Patent No.: US 12,215,380 B2
(45) Date of Patent: Feb. 4, 2025

(54) NUCLEIC ACID SEQUENCE MEASUREMENT DEVICE

(71) Applicant: Yokogawa Electric Corporation, Tokyo (JP)

(72) Inventors: Takashi Tadenuma, Tokyo (JP); Yuki Miyauchi, Tokyo (JP); Tomoyuki Taguchi, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 883 days.

(21) Appl. No.: 17/291,010

(22) PCT Filed: Oct. 18, 2019

(86) PCT No.: PCT/JP2019/041142
§ 371 (c)(1),
(2) Date: May 4, 2021

(87) PCT Pub. No.: WO2020/095657
PCT Pub. Date: May 14, 2020

(65) Prior Publication Data
US 2022/0042080 A1 Feb. 10, 2022

(30) Foreign Application Priority Data

Nov. 9, 2018 (JP) ................................ 2018-211188

(51) Int. Cl.
*C12Q 1/6818* (2018.01)
*C12Q 1/6837* (2018.01)

(52) U.S. Cl.
CPC ......... *C12Q 1/6818* (2013.01); *C12Q 1/6837* (2013.01)

(58) Field of Classification Search
None
See application file for complete search history.

(56) References Cited

U.S. PATENT DOCUMENTS

| 2004/0009514 A1 | 1/2004 | Frutos et al. |
| 2004/0023269 A1 | 2/2004 | Li et al. |
| 2011/0129828 A1 | 6/2011 | Li et al. |
| 2015/0065377 A1 | 3/2015 | Tadenuma et al. |
| 2018/0320223 A1 | 11/2018 | Lei et al. |

FOREIGN PATENT DOCUMENTS

| CA | 2323075 A1 | 9/1999 |
| CA | 2324261 A1 | 9/1999 |
| EP | 2843059 B1 * | 4/2016 |
| JP | 2002-506654 A | 3/2002 |
| JP | 2002-506656 | 3/2002 |
| JP | 2004-511227 A | 4/2004 |
| JP | 2015-043702 A | 3/2015 |
| JP | 5928906 B2 | 6/2016 |
| WO | WO2016/149694 A1 * | 9/2016 |

OTHER PUBLICATIONS

Liu et al, "Microbead-Based Platform for Multiplex Detection of DNA and Protein", ACS Applied Materials & Interfaces, 2017, vol. 9, pp. 9462-9469; Cited in International Search Report (ISR) dated Dec. 3, 2019 filed in PCT/JP2019/041142.
Tadenuma et al., "Development of a Nucleic Acid Detection System for Rapid Microbial Tests", Yokogawa Technical Report, vol. 60, No. 1, 2017, pp. 7-12; Cited in ESR.

* cited by examiner

*Primary Examiner* — Brian Gangle
*Assistant Examiner* — Lakia J Jackson-Tongue
(74) *Attorney, Agent, or Firm* — RANKIN, HILL & CLARK LLP (57) ABSTRACT

In a case where the target (30) is not supplied, binding through a nucleic acid sequence from the base end on a side of the solid phase surface of the complementary sequence complementary to a part of the nucleic acid sequence of the detection sequence to the other base end is maintained, which causes fluorescence of the fluorescent molecule (11) to be quenched by the quenching molecule (21) close to the fluorescent molecule (11). In a case where the target (30) is supplied, the target is bound to the detection sequence and the binding through the complementary sequence is released, which causes the fluorescent molecule (11) to separate from the quenching molecule (21) and emit fluorescence.

15 Claims, 9 Drawing Sheets

000
NUCLEIC ACID SEQUENCE MEASUREMENT DEVICE

TECHNICAL FIELD

The present invention relates to a nucleic acid sequence measurement device that measures a target having a specific nucleic acid sequence included in a sample by means of hybridization.

BACKGROUND ART

As a nucleic acid sequence measurement method for measuring a target having a specific nucleic acid sequence included in a sample by means of hybridization, a nucleic acid sequence measurement method with a simplified nucleic acid detection process using a fluorescent probe and a quenching probe has been reported (Patent Literature 1). In the method described in Patent Literature 1, when there is no target, the binding of the fluorescent probe and the quenching probe via the binding portion present in the fluorescent probe and the quenching probe is maintained, and the fluorescence of a quenching molecule that is close to a fluorescent molecule is quenched. On the other hand, when there is a target, the target binds to a detection portion present in the fluorescent probe or the quenching probe, which releases the binding of the probes via the binding portion, then the quenching molecule is separated from the fluorescent molecule, and as a result the fluorescent molecule emits fluorescence. By measuring the fluorescence, the target included in the sample can be measured.

CITATION LIST

Patent Literature

[Patent Literature 1]
  Japanese Patent No. 5928906

SUMMARY OF INVENTION

Technical Problem

However, in the method described in Patent Literature 1, the fluorescent probe with a fluorescent molecule added binds to the quenching probe with the quenching molecule added at binding portions present in portions of the fluorescent probe and the quenching probe having nucleic acid sequences complementary to each other. Thus, because it is hard to say that the binding force of the fluorescent probe and the quenching probe is weak and the quenching molecule sufficiently suppresses fluorescence, fluorescence when there is no target, in other words, offset light, tends to increase. If an amount of offset light is great and targets are at a low concentration, it is hard to identify change in fluorescence, which deteriorates detection sensitivity.

In addition, in the method described in Patent Literature 1, a length of the nucleic acid sequence of the binding portion present in portions of the fluorescent probe and the quenching probe with nucleic acid sequences complementary to each other needs to be appropriately decided. For this reason, if the nucleic acid sequence of the binding portion is too short, it is not possible to bind the fluorescent probe to the quenching probe via the binding portion, and not possible to quench the fluorescent probe with the quenching probe. Conversely, if the nucleic acid sequence of the binding portion is too long, binding of the fluorescent probe to the quenching probe via the binding portion becomes too strong, the fluorescent probe and the quenching probe remain bound and are not separated from each other even if a target is supplied, and thus it is not possible to measure the target included in the sample.

Therefore, an objective of the present invention is to provide a nucleic acid sequence measurement device that has excellent detection sensitivity by decreasing offset light when there is no target and can detect a target without relying on a length of a binding portion of a fluorescent probe and a quenching probe.

Solution to Problem

The present invention employs the following configurations to achieve the above-described objective.

[1] A nucleic acid sequence measurement device that measures a target having a specific nucleic acid sequence included in a sample by means of hybridization, the nucleic acid sequence measurement device including a fluorescent probe with a fluorescent molecule added at a predetermined position, a quenching probe with a quenching molecule added at a predetermined position, and a substrate having a solid phase surface to which a base end of each of the fluorescent probe and the quenching probe is fixed, wherein one of the fluorescent probe and the quenching probe has a detection sequence having a nucleic acid sequence complementary to a nucleic acid sequence of the target, the other one of the fluorescent probe and the quenching probe has a nucleic acid sequence complementary to a nucleic acid sequence of a part of the detection sequence (which will also be referred to as a complementary sequence) and a nucleic acid sequence from a base end of the complementary sequence on the solid phase surface side to the other base end is complementary to the part of the detection sequence, the fluorescent probe or the quenching probe having the detection sequence has a longer nucleic acid sequence than the fluorescent probe or the quenching probe having the complementary sequence, and the base end of the fluorescent probe and the base end of the quenching probe are fixed to the solid phase surface so that a positional relationship in which fluorescence emitted by the fluorescent molecule is quenched by the quenching molecule close to the fluorescent molecule is established.

[2] The nucleic acid sequence measurement device described in [1], wherein, in a case where hybridization of the target and the detection sequence does not occur, binding of the fluorescent probe and the quenching probe is maintained, which causes fluorescence emitted by the fluorescent molecule to be quenched by the quenching molecule close to the fluorescent molecule, and in a case where hybridization of the target and the detection sequence occurs, binding of the fluorescent probe and the quenching probe is released, which causes the fluorescent molecule to separate from the quenching molecule and emit fluorescence.

[3] The nucleic acid sequence measurement device described in [1] or [2], wherein the quenching probe has the detection sequence.

[4] The nucleic acid sequence measurement device described in any one of [1] to [3], wherein the substrate is a flat plate, and the solid phase surface is one plane of the flat plate.

[5] The nucleic acid sequence measurement device described in any one of [1] to [3], wherein the substrate is a bead, and the solid phase surface is a surface of the bead.

[6] The nucleic acid sequence measurement device described in any one of [1] to [5], wherein a number of quenching probes is greater than a number of fluorescent probes.

[7] The nucleic acid sequence measurement device described in any one of [1] to [5], wherein a number of fluorescent probes is greater than a number of quenching probes.

[8] The nucleic acid sequence measurement device described in any one of [1] to [7], wherein a number of quenching molecules is greater than a number of fluorescent molecules.

[9] The nucleic acid sequence measurement device described in [8], wherein a ratio of the number of fluorescent molecules to the number of quenching molecules is 2:3.

[10] The nucleic acid sequence measurement device described in any one of [1] to [9], wherein the predetermined position at which the fluorescent molecule is added is in the middle of the fluorescent probe.

[11] The nucleic acid sequence measurement device described in any one of [1] to [9], wherein the predetermined position at which the quenching molecule is added is in the middle of the quenching probe.

[12] The nucleic acid sequence measurement device described in any one of [1] to [11], wherein a number of predetermined positions at which the fluorescent molecule is added is multiple.

[13] The nucleic acid sequence measurement device described in any one of [1] to [11], wherein a number of predetermined positions at which the quenching molecule is added is multiple.

[14] The nucleic acid sequence measurement device described in [12], wherein multiple fluorescent molecules of different types are added at the predetermined positions.

[15] The nucleic acid sequence measurement device described in [13], wherein multiple quenching molecules of different types are added at the predetermined positions.

More features and aspects of the present invention will be apparent with reference to accompanying drawings and in detailed description of the embodiments which will be described below.

Advantageous Effects of Invention

According to the nucleic acid sequence measurement device of the present invention, the fluorescent probe and the quenching probe bind to each other in the nucleic acid sequence portion from the base end of the complementary sequence on the solid phase surface side to the other base end, and thus the nucleic acid sequence measurement device can exhibit an excellent quenching effect and reduce offset light compared to a nucleic acid sequence measurement device of the related art in which a probe with a fluorescent molecule added thereto and a quenching probe with a quenching molecule added thereto bind to each other in a binding portion present in a portion of the fluorescent probe and the quenching probe in which the probes are complementary to each other. Thus, the minimum amount of light which can be detected can be reduced, and the detection sensitivity can be improved.

In addition, the fluorescent probe or the quenching probe having the detection sequence has a longer nucleic acid sequence than the fluorescent probe or the quenching probe having the complementary sequence, and thus a binding force of the fluorescent probe or the quenching probe having the detection sequence and a target is stronger than a binding force of the fluorescent probe and the quenching probe binding in the complementary sequence. Thus, the fluorescent probe or the quenching probe having the detection sequence can be separated from the fluorescent probe or the quenching probe having the complementary sequence, and bind to a target.

In addition, according to the nucleic acid sequence measurement device of the present invention, because the fluorescent probe and the quenching probe bind to each other in the nucleic acid sequence portion from the base end of the complementary sequence on the solid phase surface side to the other base end, a fluorescent probe and a quenching probe that enable a target to be detected can be easily designed, compared to the nucleic acid sequence measurement device of the related art in which the detection of a target relies on a length of a nucleic acid sequence of a binding portion of the fluorescent probe and the quenching probe.

In addition, according to the nucleic acid sequence measurement device, because the base ends of the fluorescent probe and the quenching probe with molecules independent of each other are fixed to the substrate, the quenching effect can be appropriately exhibited, satisfactory detection sensitivity can be obtained, a labeling process is unnecessary, and a washing process can be omitted. By making the labeling process unnecessary and omitting the washing process, time and effort required for an experiment of hybridization can be further reduced, and working time and cost can be cut. Furthermore, degraded performance caused by inadequacies in the washing process, a reduced amount of light, an increased intensity of offset light, occurrence of variation, or the like can be avoided. Accordingly, more uniform results can be obtained on an array surface, and detection reproducibility is also improved.

Furthermore, according to the nucleic acid sequence measurement device of the present invention, hybridization can be observed in real time. In other words, hybridization can be observed in a state in which a solution containing detection target molecules (targets) is added to a nucleic acid sequence measurement device of a DNA array, or the like (a wet state). Accordingly, an amount of light without the influence of washing can be checked and hybridization can be observed in real time. Thus, the hybridization can be finished in a shorter period of time depending on a situation, like when a sample concentration is high and the hybridization progresses rapidly, or the like.

DESCRIPTION OF EMBODIMENTS

A nucleic acid sequence measurement device of the present invention performs measurement on a target having a specific nucleic acid sequence included in a sample by means of hybridization, the nucleic acid sequence measurement device including a fluorescent probe with a fluorescent molecule added at a predetermined position, a quenching probe with a quenching molecule added at a predetermined position, and a substrate having a solid phase surface to which a base end of each of the fluorescent probe and the quenching probe is fixed, in which one of the fluorescent probe and the quenching probe has a detection sequence having a nucleic acid sequence complementary to a nucleic acid sequence of the target, the other one of the fluorescent probe and the quenching probe has a nucleic acid sequence complementary to a nucleic acid sequence of a part of the detection sequence (which will also be referred to as a "complementary sequence"), a nucleic acid sequence from a base end of the complementary sequence on the solid phase surface side to the other base end is complementary to a part of the detection sequence, the fluorescent probe or the quenching probe having the detection sequence has a longer nucleic acid sequence than the fluorescent probe or the quenching probe having the complementary sequence, and the base end of the fluorescent probe and the base end of the quenching probe are fixed to the solid phase surface so that a positional relationship in which fluorescence emitted by the fluorescent molecule is quenched by the quenching molecule close to the fluorescent molecule is established.

Embodiments of a nucleic acid sequence measurement device of the present invention will be described below.

Figure 1:
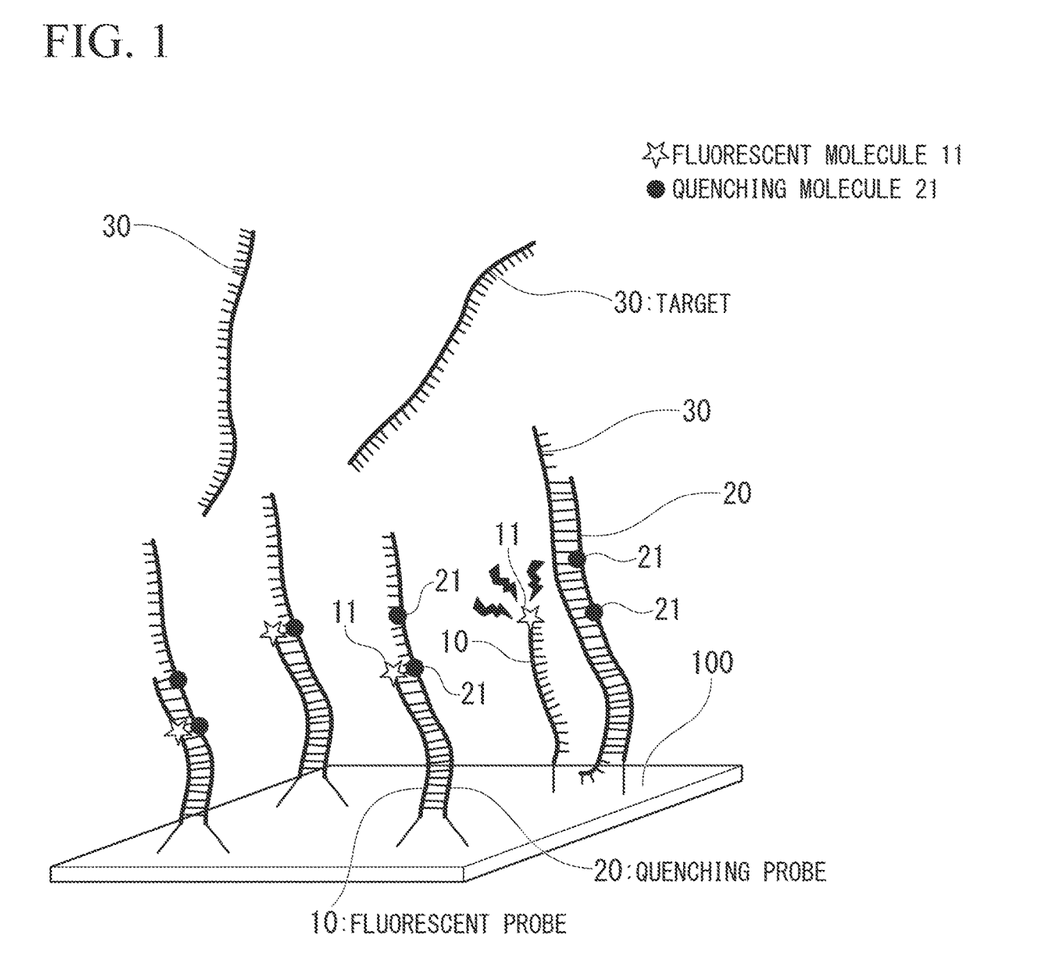
FIG. 1 is a diagram illustrating a configuration of a nucleic acid sequence measurement device according to the present invention.
Figure 2:
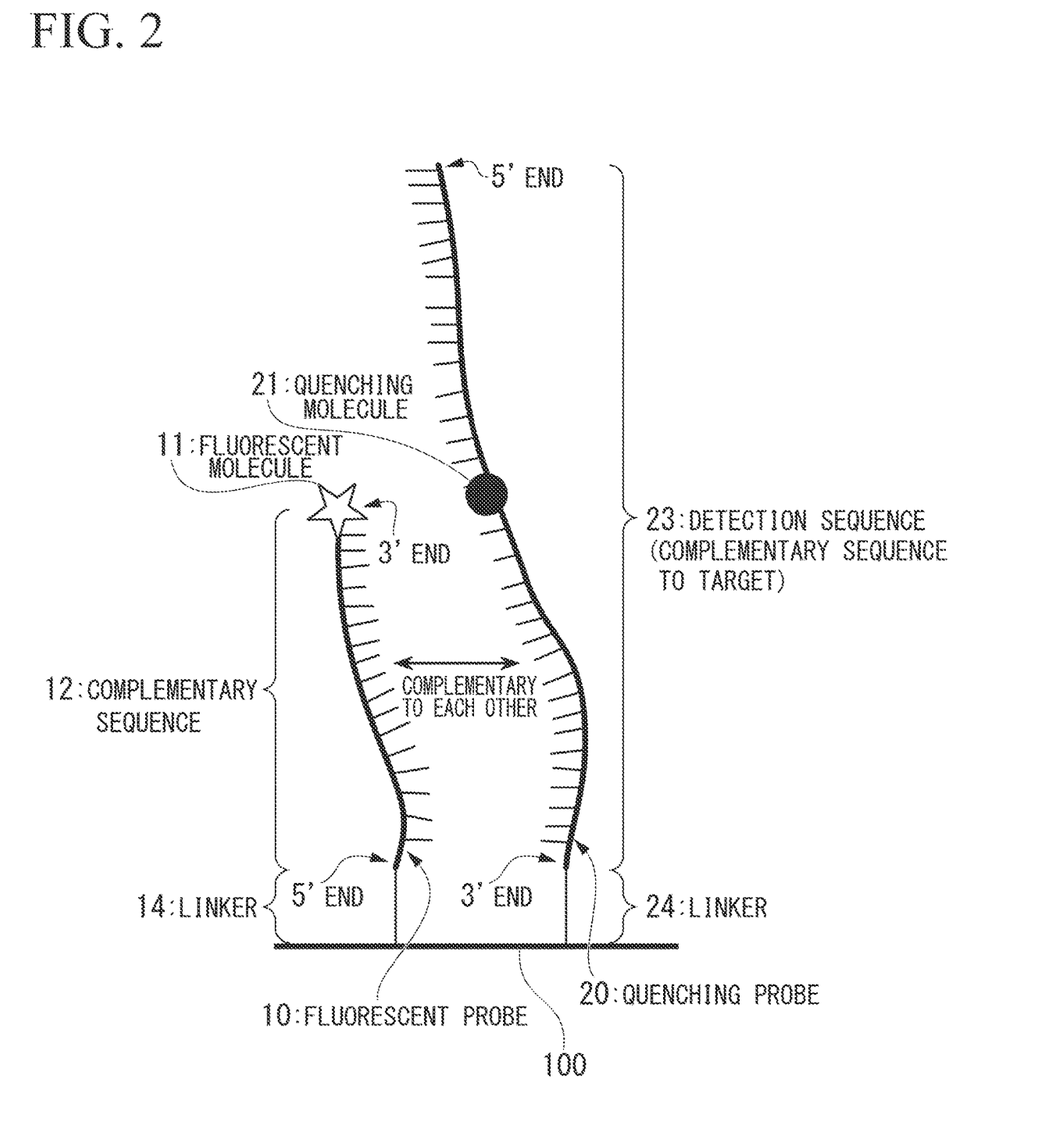
FIG. 2 is a diagram illustrating a configuration example of probes.

FIG. 1 is a diagram illustrating a configuration of a nucleic acid sequence measurement device of the present invention, and FIG. 2 is a diagram illustrating a configuration example of probes.

The nucleic acid sequence measurement device of the present embodiment is configured such that a quenching probe 20 obtained by adding a quenching molecule 21 to a detection sequence 23 that is a complementary sequence to a target 30, which is a nucleic acid to be detected, and a fluorescent probe 10 obtained by adding a fluorescent substance 11 to a complementary sequence 12 that is a sequence complementary to a part of the detection sequence 23 are fixed to a solid phase surface 100 such as a substrate as illustrated in FIGS. 1 and 2 to establish a positional relationship in which the quenching molecule 21 close to the fluorescent molecule 11 quenches the fluorescence emitted by the fluorescent molecule 11. The nucleic acid sequence of the detection sequence 23 is longer than that of the complementary sequence 12.

In the present invention, the principle of quenching with fluorescence resonance energy transfer is used. Although the fluorescent molecule 11 is not particularly limited, a known substance, for example, EDANS, Coumarin, FAM, FITC, Cy2, TF2, TF3, HEX, JOE, TET, Cy3, Cy5, Alexa Fluor™ (a registered trademark) 532, Alexa Fluor™ (a registered trademark) 610, Alexa Fluor™ (a registered trademark) 647, ATTO532, ATTO633, Qdot™ (a registered trademark) 565, Qdot™ (a registered trademark) 585, Qdot™ (a registered trademark) 605, Qdot™ (a registered trademark) 705, iFluor™ 532, iFluor™ 647, or the like may be used. Although the quenching molecule 21 is not particularly limited, a known substance, for example, Dabcyl, TQ1, TQ2, TQ3, Eclipse™ (a registered trademark), BHQ1, BHQ2, BHQ3, Cy5Q, Cy7Q, Iowa Black™ (a registered trademark) FQ, Iowa Black™ (a registered trademark) RQ, IRDye QC-1, QSY7, QSY21, QXL570, QXL570, QXL570, or the like may be used. Although a combination of the fluorescent molecule 11 and the quenching molecule 21 is not particularly limited, for example, a combination of EDANS, Coumarin, or TF2 with Dabcyl or TQ1, a combination of FAM, FITC, TET, Alexa Fluor™ (a registered trademark) 532, Cy2, Cy3, TF2 or TF3 with TQ2, a combination of Alexa Fluor™ (a registered trademark) 532, Cy3, HEX, JOE, TF2, TF3, TF4, or TET with TQ3, a combination of Alexa Fluor™ (a registered trademark) 532, TF2, Cy3, FAM, or HEX with Eclipse™ (a registered trademark), a combination of Alexa Fluor™ (a registered trademark) 532, TF2, TF3, Cy3, FAM, HEX, TET, or Cy3 with BHQ1, a combination of TF3, TF4, Cy3, Cy5, or HEX with BHQ2, a combination of Cy5, Alexa Fluor™ (a registered trademark) 647, or TF5 with Iowa Black™ (a registered trademark) RQ, IRDye QC-1, QSY21, TQ4, TQ5, BHQ2 or BHQ3, a combination of Cy3, TF3, or TF4 with Cy5Q, Iowa Black™ (a registered trademark) FQ, Iowa Black™ (a registered trademark) RQ, IRDye QC-1, QSY7, or QXL570, a combination of Alexa Fluor™ (a registered trademark) 532 with Cy5Q, TQ2, TQ3, Iowa Black™ (a registered trademark) FQ, Iowa Black™ (a registered trademark) RQ, IRDye QC-1, QSY7, or QXL570, a combination of TF3 with BHQ1, BHQ2, or Cy5Q, or the like may be used.

The fluorescent probe 10 includes the complementary sequence 12 and a linker 14 as illustrated in FIG. 2. The complementary sequence 12 is provided from the 3' end of the fluorescent probe 10. The nucleic acid sequence from the 3' end to the 5' end of the fluorescent probe 10 is a complementary sequence to the nucleic acid sequence from the 3' end of the detection sequence 23 of the quenching probe 20 on the solid phase surface 100 to the portion thereof corresponding to the 3' end of the fluorescent probe 10. The linker 14 is connected to the 5' end of the complementary sequence 12 and continues to the solid phase surface 100. The fluorescent molecule 11 is added to the 3' end of the fluorescent probe 10.

The quenching probe 20 has the detection sequence 23 and a linker 24. The detection sequence 23 is provided from the 5' end of the quenching probe 20. The linker 24 is connected to the 3' end of the detection sequence 23 and continues to the solid phase surface 100. The quenching molecule 21 is fixed at a position close to the fluorescent molecule 11 added to the fluorescent probe 10. A length of the nucleic acid sequence of the detection sequence 23 of the quenching probe 20 is longer than that of the complementary sequence 12.

The fluorescent probe 10 and the quenching probe 20 are fixed to the solid phase surface 100 via the linker 14 and the linker 24, respectively. In addition, the nucleic acid sequence from the base end (the 5' end) of the fluorescent probe 10 on the solid phase surface 100, the base end being connected to the linker 14, to the other base end (the 3' end) is complementary to the nucleic acid sequence from the end (the 3' end) of the detection sequence 23 of the quenching probe 20 on the solid phase surface 100, the end being connected to the linker 24, to the portion thereof corresponding to the 3' end of the fluorescent probe 10.

Further, being complementary in the present invention means having a nucleic acid sequence that can form a double chain state with another nucleic acid sequence, and may not necessarily be completely complementary, and may include a few mismatched base pairs.

In addition, the fluorescent probe 10 and the quenching probe 20 are fixed to the solid phase surface 100 at a position at which the fluorescent probe 10 and the quenching probe 20 can bind to each other. In addition, when the fluorescent probe 10 and the quenching probe 20 bind to each other, the quenching molecule 21 gets close to the fluorescent molecule 11, and as a result, the fluorescent probe 10 and the quenching probe 20 are disposed in a state in which the fluorescent molecule 11 is quenched.

Figure 3:
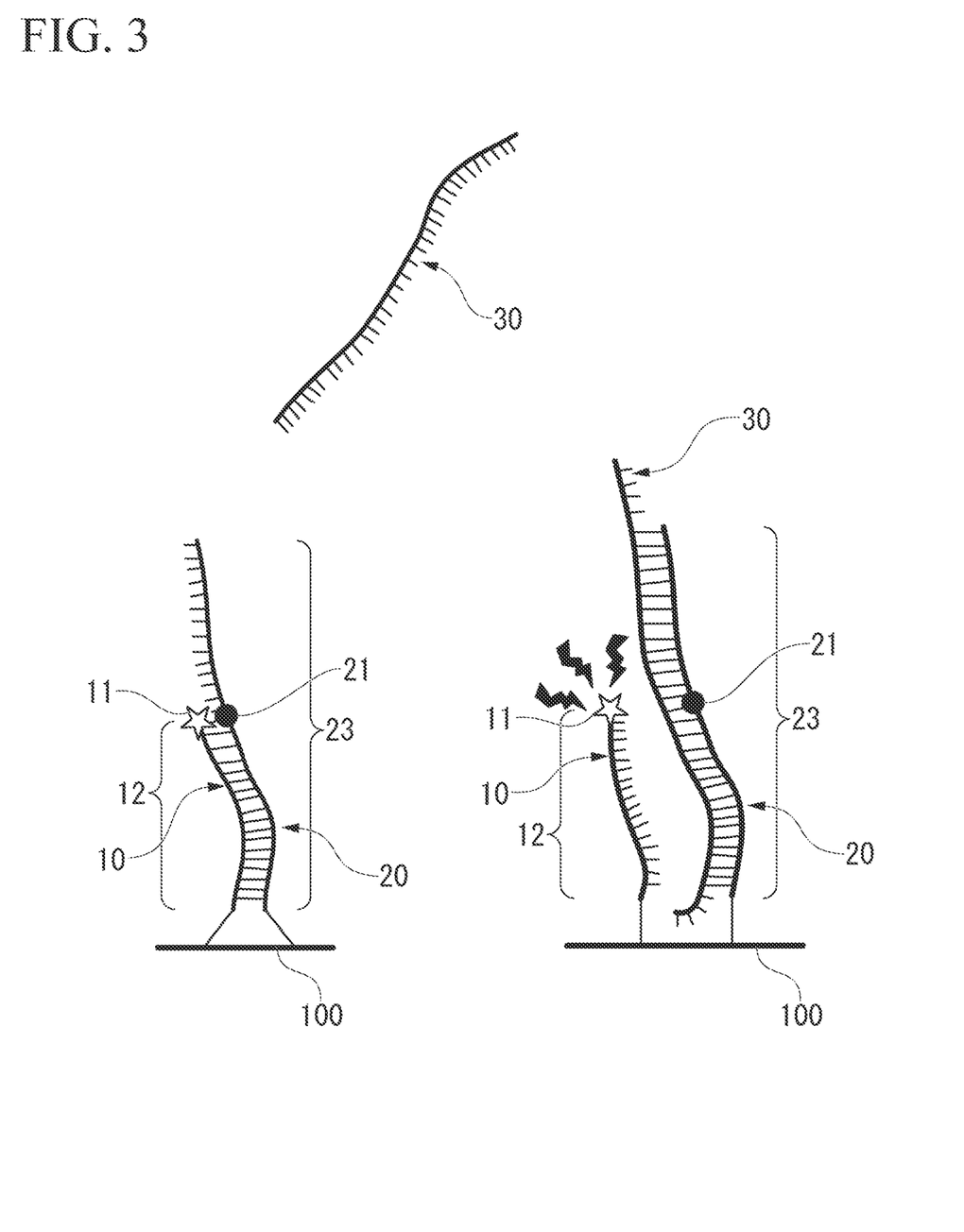
FIG. 3 is a diagram schematically illustrating the principle of detecting a target.

Next, the principle and the operation procedure for detecting a target 30 using the nucleic acid sequence measurement device will be described. FIG. 3 is a diagram schematically illustrating the principle of detecting a target, and FIG. 4 is a diagram illustrating the operation procedure for detecting a target.

When there is no target 30, the fluorescent probe 10 with the fluorescent molecule 11 added and the quenching probe 20 with the quenching molecule 21 added bind to each other as illustrated in FIG. 3. Thus, the fluorescent molecule 11 and the quenching molecule 21 get close to each other. In this state, even if the fluorescent molecule 11 is irradiated with excitation light, the fluorescent molecule does not emit fluorescence due to the influence of the quenching molecule 21.

Figure 4:
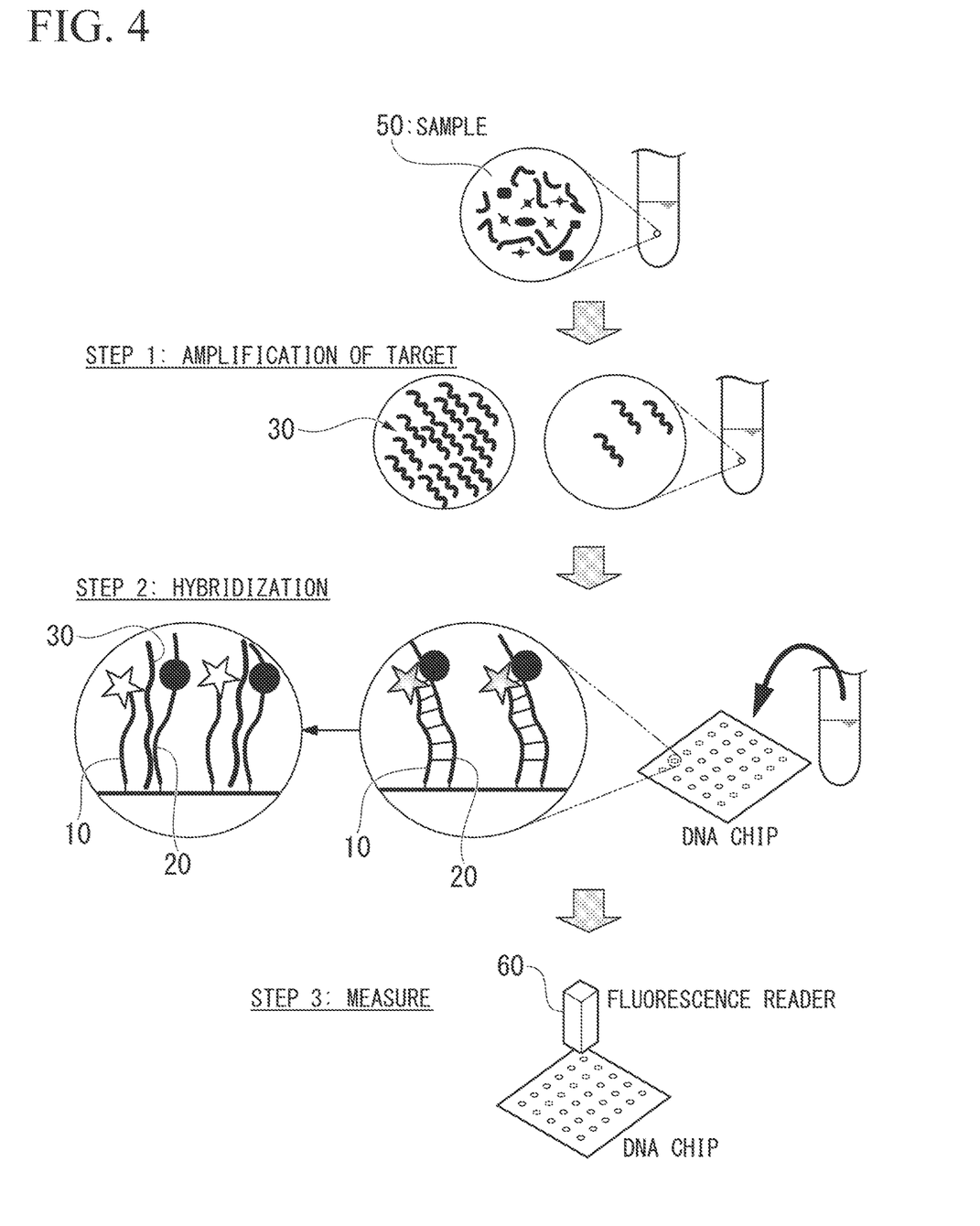
FIG. 4 is a diagram illustrating an operation procedure for detecting a target.

Genes (targets 30) of a sample 50 are amplified (step 1) as illustrated in FIG. 4. Next, a solution containing the amplified targets 30 is supplied onto the solid phase surface 100 of a DNA chip to carry out hybridization (step 2).

The nucleic acid sequence of the detection sequence 23 of the quenching probe 20 that is a complementary nucleic acid sequence to the nucleic acid sequence of the targets 30 is longer than the complementary sequence 12 of the fluorescent probe 10 as illustrated in FIG. 3. For this reason, a binding force of the quenching probe 20 having the detection sequence 23 and a target 30 is stronger than a binding force of the fluorescent probe 10 and the quenching probe 20 bound in the portion of the complementary sequence 12. Thus, when there is a target 30, the quenching probe 20 having the detection sequence 23 is separated from the fluorescent probe 10 and binds to the target 30. When the target 30 binds to the fluorescent probe 10, the fluorescent probe 10 is unbound from the quenching probe 20, causing the distance between the quenching molecule 21 and the fluorescent molecule 11 to be longer and the quenching state to be released, and thus the fluorescent molecule 11 emits fluorescence as the molecule is irradiated with excitation light. Thus, when the solid phase surface 100 is observed using a fluorescence reader 60 as illustrated in FIG. 4, it is possible to confirm the presence of a target nucleic acid (the target 30) in the sample based on whether the fluorescent probe 10 emits fluorescence (step 3). In addition, at this time, the target 30 that is contained in the solution and has not been captured does not need to be washed away because the target does not emit fluorescence. Thus, when a target is present in the solution, the solid phase surface 100 can be observed through the solution. Therefore, the amount of light without the influence of washing can be measured, and real-time measurement is also possible during the hybridization.

In the stage in which genes have been amplified (step 1), a test for checking whether the genes have been amplified may be performed, and hybridization (step 2) may be carried out only when the genes have been amplified.

Further, a timing at which the presence of genes is inspected is not limited to a time after the amplification, and may be during the amplification reaction. As a technique for the inspection, electrophoresis, antigen-antibody reaction, mass spectrometry, a real-time PCR method, or the like can be appropriately used.

In addition, the nucleic acid (the target 30) may bind to a protein, a sugar chain, or the like. In this case, an interaction of the protein, the sugar chain, or the like with the nucleic acid (the target 30) can be confirmed.

The nucleic acid sequence measurement device of the present invention is not limited to the above-described embodiment, and various modifications as follows can be made.

Quenching efficiency in the quenching state can be controlled by changing the presence ratios of the fluorescent probe modified with a phosphor and the quenching probe modified with a quenching molecule and fixing each of the probes. If the number of quenching probes is greater than the number of fluorescent probes, the probability of the number of fluorescent molecules being coupled increases, and thus quenching efficiency increases. Thus, offset light can be suppressed to be low in amount. In addition, if the number of fluorescent probes is greater than the number of quenching probes, the probability of fluorescent probes being affected by the quenching action becomes low, and thus the amount of fluorescence (an amount of hybridization light) emitted after detection of a target substance becomes greater.

The detection sequence has a longer nucleic acid sequence than the complementary sequence. A length of the detection sequence is not particularly limited as long as it is longer than a length of the complementary sequence, and may be longer than a length of the complementary sequence by, for example, one base or more, five bases or more, or ten bases or more.

Figure 5:
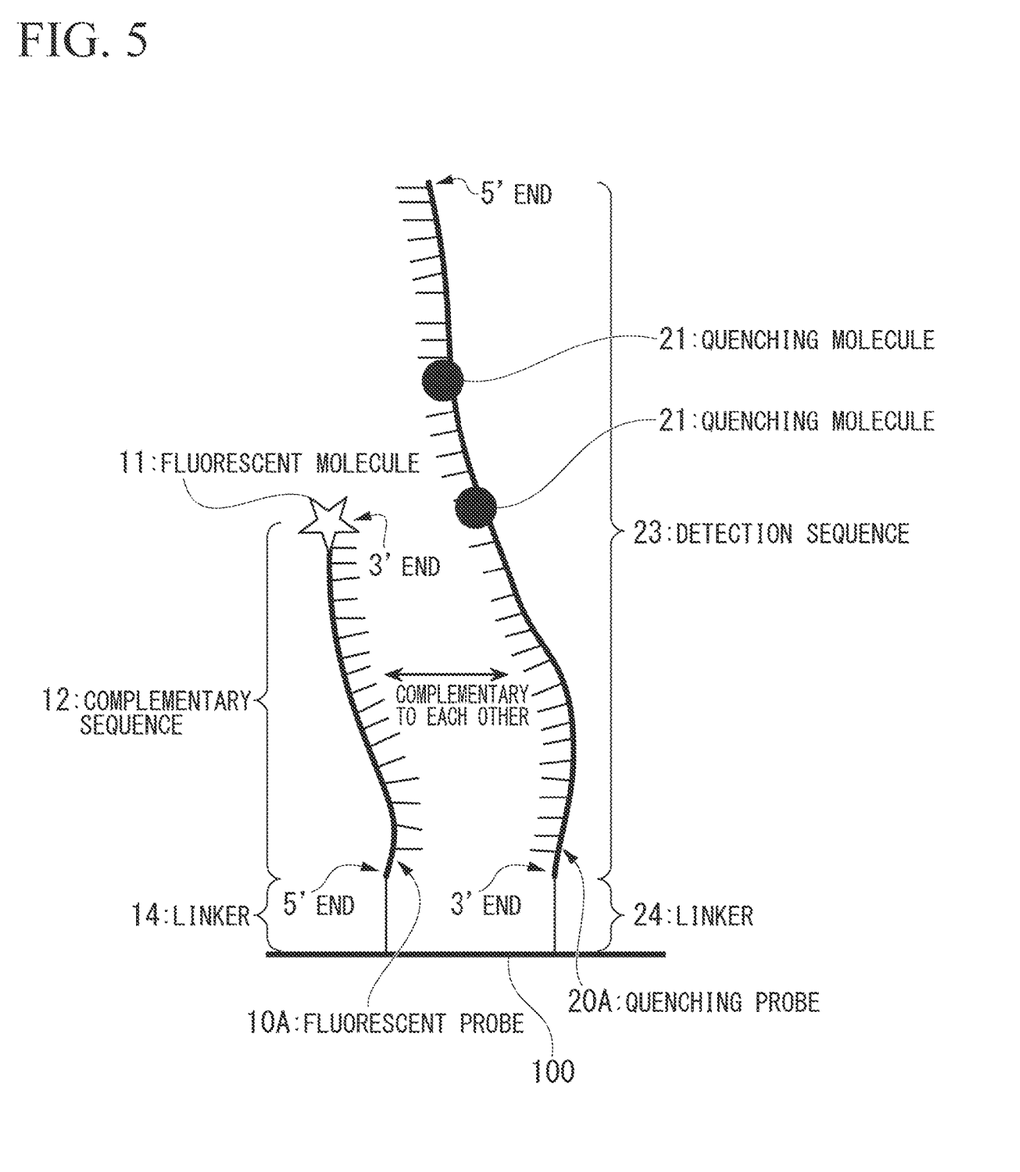
FIG. 5 is a diagram illustrating a modified example and diagram illustrating an example in which quenching molecules are added at multiple locations.
Figure 6:
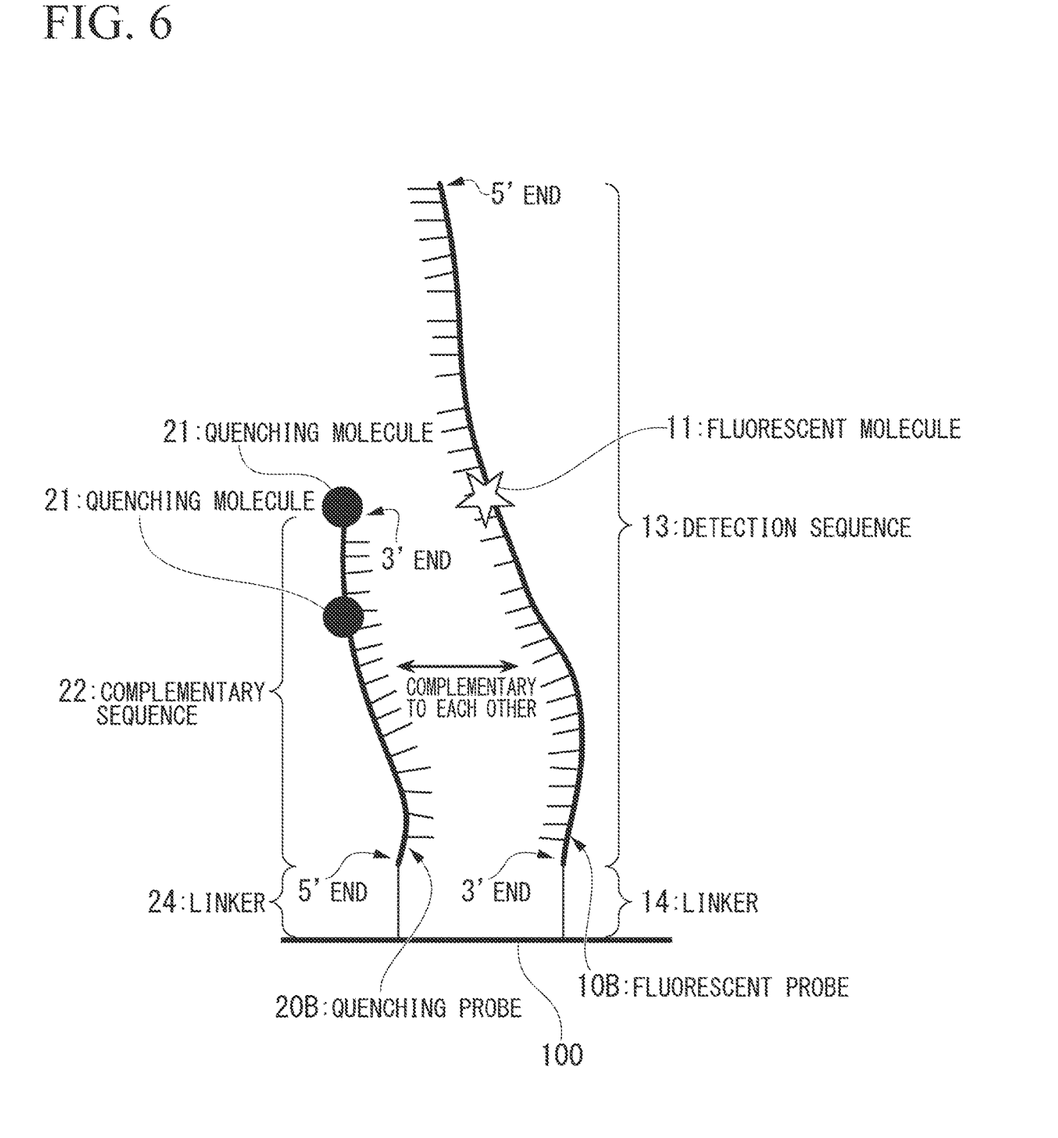
FIG. 6 is a diagram illustrating a modified example and diagram illustrating an example in which a detection sequence has been imparted to a fluorescence probe.
Figure 7:
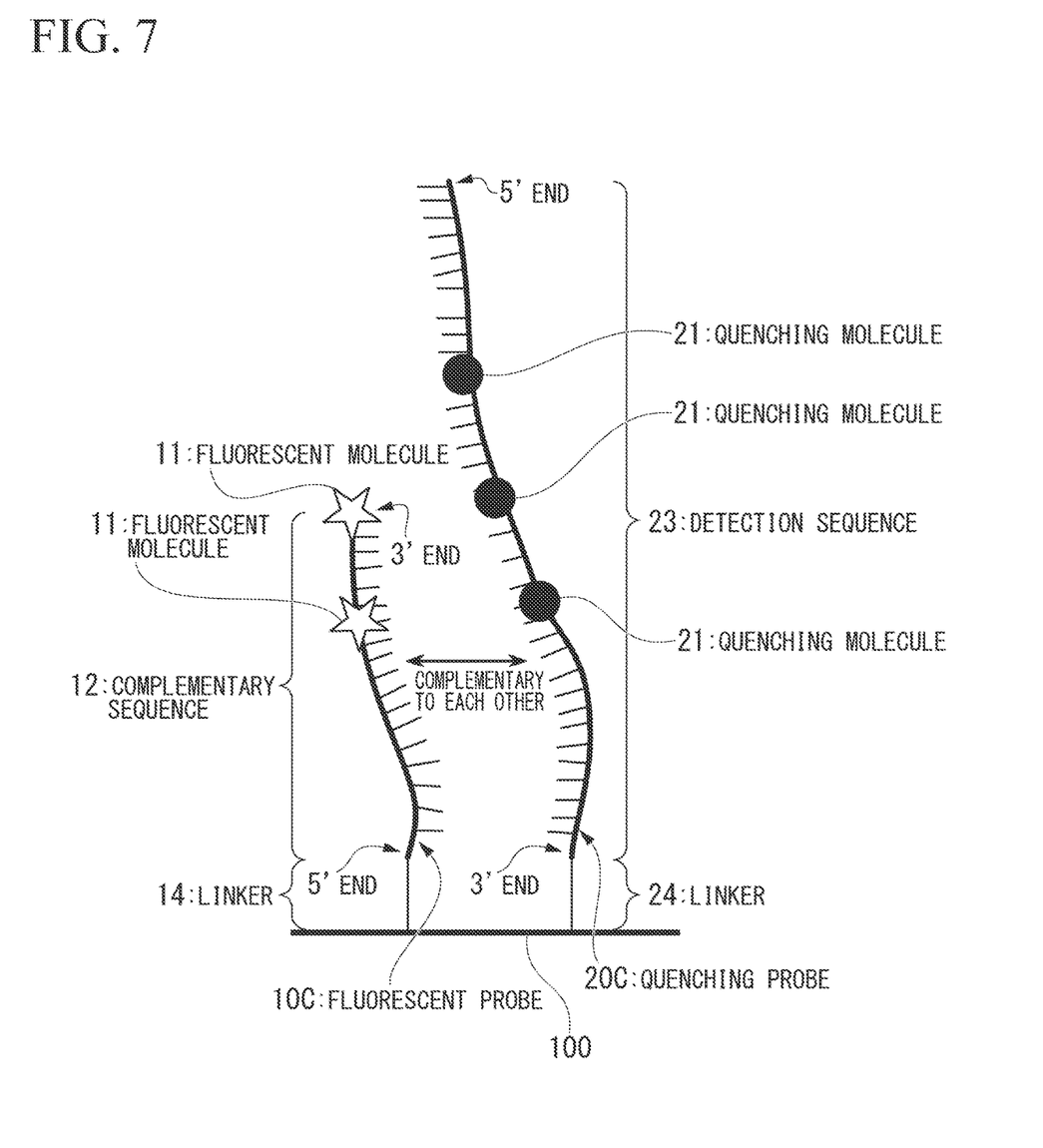
FIG. 7 is a diagram illustrating a modified example and diagram illustrating an example in which fluorescent molecules and quenching molecules are added at multiple locations.

The fluorescent molecule or the quenching molecule may not be attached to a tip end of a probe, and the fluorescent molecule or the quenching molecule may be added at a position in the middle of the probes as illustrated in FIGS. 5 to 7. In the example of FIG. 5, quenching molecules 21 are added in the middle of a quenching probe 20A. In the example of FIG. 6, a fluorescent molecule 11 is added in the middle of a fluorescent probe 10B. In the example of FIG. 7, fluorescent molecules 11 and quenching molecules 21 are added in the middle of each of a fluorescent probe 10C and a quenching probe 20C. However, it is desirable to design the quenching molecules 21 and the fluorescent molecules 11 to be located at a position at which the quenching molecules get close to the fluorescent molecules and the molecules face each other to bring the quenching action in a state in which the fluorescent probes 10A to 10C and the quenching probes 20A to 20C bind to each other, respectively. In a case where a fluorescent molecule or a quenching molecule is added at a position other than a tip end of a probe, there is an advantage that another modification can be applied to the tip end of the probe.

Multiple types of fluorescent molecules and quenching molecules may be added at multiple locations. FIGS. 5 and 6 are diagrams illustrating an example in which quenching molecules are added at multiple locations. In the example of FIG. 5, the fluorescent molecule 11 is added to the fluorescent probe 10A, and the quenching molecules 21 and 21 are added to the quenching probe 20A. In the example of FIG.

6, the fluorescent molecule 11 is added to the fluorescent probe 10B, and the quenching molecules 21 and 21 are added to the quenching probe 20B. In a case where multiple quenching molecules are added to one probe, types of the quenching molecules may vary. In a case where multiple quenching molecules are added to one probe, the quenching effect of the quenching molecules with respect to a fluorescent molecule can be increased, and thus the amount of offset light can be reduced. Thus, the minimum amount of light which can be detected can be reduced, and thus the detection sensitivity can be improved.

FIG. 7 is a diagram illustrating an example in which fluorescent molecules and quenching molecules are added at multiple locations. In the example of FIG. 7, two fluorescent molecules 11 and 11 are added to the fluorescent probe 10C, and three quenching molecules 21, 21, and 21 are added to the quenching probe 20C. In a case where multiple fluorescent molecules and multiple quenching molecules are added to each one probe, types of the fluorescent molecules and the quenching molecules may vary. In the case where multiple fluorescent molecules and multiple quenching molecules are added to each one probe, an amount of fluorescence when a target binds increases, and detection can be performed with higher sensitivity. In addition, by increasing the number of quenching molecules and the number of fluorescent molecules, the amount of offset light when there is no target can be reduced.

The detection sequence may be provided in the quenching probe or the fluorescent probe. In a case where the quenching probe has the detection sequence, the target 30 binds to the detection sequence of the quenching probe as described above. On the other hand, in a case where the fluorescent probe has the detection sequence, the target 30 binds to the detection sequence of the fluorescent probe.

FIG. 6 is a diagram schematically illustrating a state in which a detection sequence has been imparted to the fluorescent probe and multiple quenching molecules 21 and 21 are added to the quenching probe. By adding multiple quenching molecules to the quenching probe as illustrated in FIG. 6, the amount of offset light when there is no target can be reduced. In addition, because the binding force of the target and the fluorescent probe is stronger than the binding force of the fluorescent probe and the quenching probe, the fluorescent probe is separated from the quenching probe when there is a target and can bind to the target, and thus fluorescent molecules can emit fluorescence.

In addition, a substrate to which the fluorescent probe and the quenching probe are fixed may be a flat plate or a bead. In a case where the substrate is a flat plate, the solid phase surface to which the fluorescent probe and the quenching probe are fixed can be one plane of the flat plate. In a case where the substrate is a bead, the solid phase surface to which the fluorescent probe and the quenching probe are fixed can be a surface of the bead. If the fluorescent probe and the quenching probe are fixed to the surface of the bead, the fluorescent probe and the quenching probe form a shape in which the probes radially expand from the bead. In this case, the surface area of the solid phase surface to which the probes are fixed increases, and the number of probes per unit area can be increased. In addition, detection target molecules can be selectively collected by collecting beads that have captured the detection target molecules by their size, magnetism, or the like. The collected molecules can be used for other tests, and the like in post-processes.

Next, a method for producing the nucleic acid sequence measurement device using a nucleic acid sequence measurement method of the present invention will be described.

(1) Preparation of a Solution

First, a probe solution in which fluorescent probes 10 and quenching probes 20 are mixed is prepared, and a probe concentration is adjusted.

(2) Coupling

Next, after the probe solution is heated, the probe solution is rapidly cooled, and the fluorescent probes 10 and the quenching probes 20 are coupled. Accordingly, the fluorescent probes 10 and the quenching probes 20 bind to each other in the portions of the complementary sequences of either the fluorescent probes 10 or the quenching probes 20. Here, after the probe solution is heated to 95° C., the temperature is kept for 5 minutes, then the solution is rapidly cooled to 25° C., and thereby the fluorescent probes 10 and the quenching probes 20 are coupled.

(3) Fixation to a Solid Phase Surface

Next, the probe solution in which the fluorescent probes 10 and the quenching probes 20 are coupled is dripped on spots on a solid phase surface to fix the fluorescent probes 10 and the quenching probes 20 to the solid phase surface 100.

(4) Washing

Next, the solid phase surface 100 is washed to remove unfixed excess probes. Through the above procedure, a nucleic acid sequence measurement device is produced.

As described above, because the fluorescent probes 10 and the quenching probes 20 bind to the solid phase surface 100 while binding to each other in the portion of the complementary sequence of either the fluorescent probes 10 or the quenching probes 20, a positional relationship of the fluorescent probes 10 and the quenching probes 20 can be appropriately managed, and the quenching effect can be appropriately exhibited. Thus, satisfactory detection sensitivity can be achieved.

A range in which the present invention is applied is not limited to the above embodiment. The present invention can be broadly applied to a nucleic acid sequence measurement device that measures a target having a specific nucleic acid sequence included in a sample by means of hybridization.

EXAMPLES

Although the present invention will be described in more detail based on examples and comparative examples, the present invention is not limited thereto.

Example 1

A probe solution in which a fluorescent probe 1 having a linker sequence, a detection sequence of a length 33 of a nucleic acid sequence, and a fluorescent molecule binding thereto had been mixed with a quenching probe 1 having a linker sequence, a complementary nucleic acid sequence to the portion of 28 bases from the base end of the detection sequence of the fluorescent probe 1 on a solid phase surface side, and a quenching molecule binding thereto was prepared.

Next, after the probe solution was heated to 95° C., the temperature was kept for 5 minutes, then the solution was rapidly cooled to 25° C., and thereby the fluorescent probe 1 and the quenching probe 1 were coupled. Accordingly, the fluorescent probe 1 and the quenching probe 1 bound to each other in the portion of the complementary sequence of the quenching probe 1. Further, a quenching molecule bound to the quenching probe 1 at the base end on the side opposite to the base end of the quenching probe 1 on the solid phase surface side, and a fluorescent molecule bound to the fluorescent probe 1 at the position of the same height as the height of the quenching molecule of the quenching probe 1 from the solid phase surface.

Next, the probe solution in which the fluorescent probe 1 and the quenching probe 1 were coupled was dripped on a spot on the solid phase surface, and the fluorescent probe 1 and the quenching probe 1 were fixed to the solid phase surface.

Figure 8:
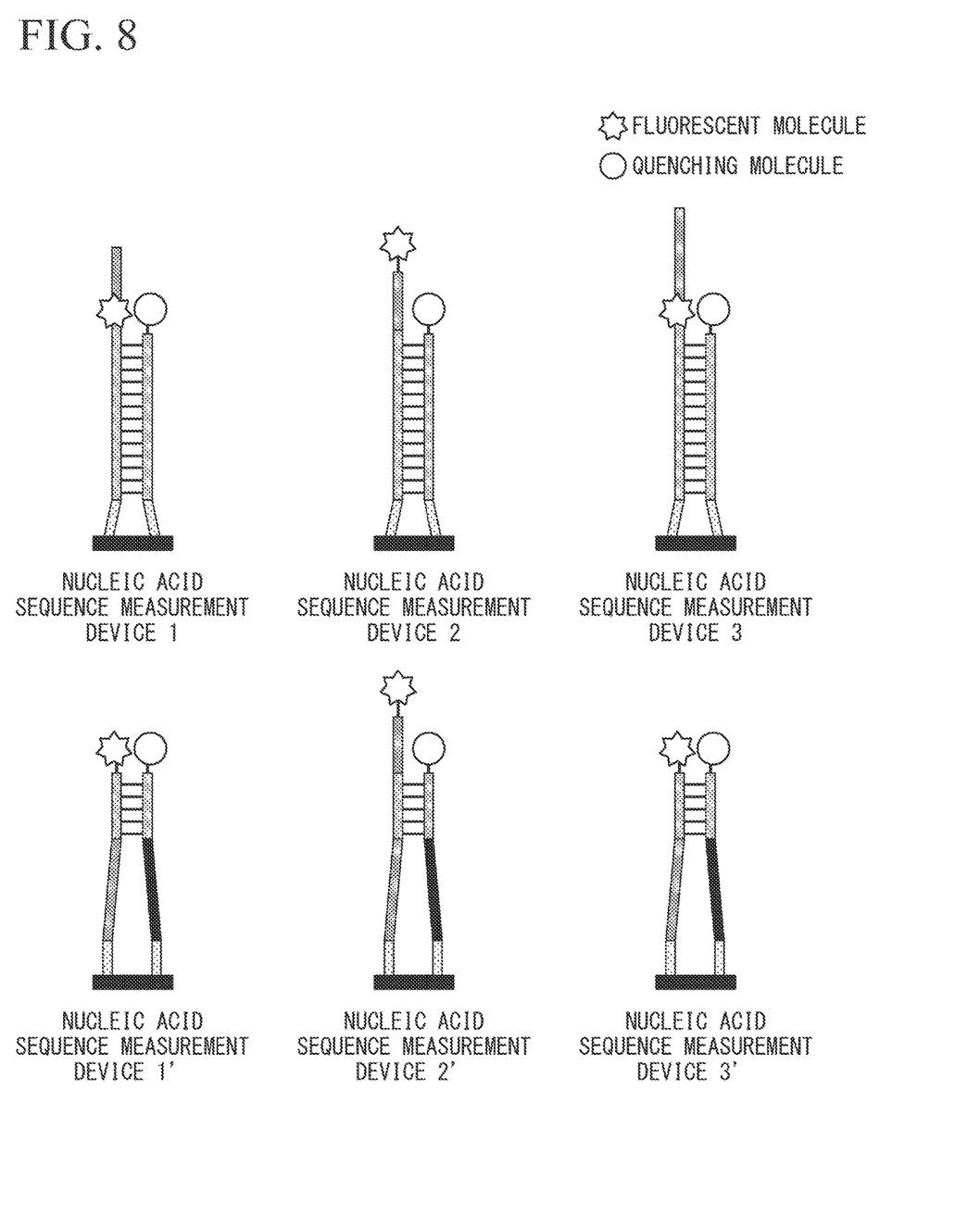
FIG. 8 includes diagrams schematically illustrating structures of nucleic acid sequence measurement devices of Examples 1 to 3 and nucleic acid sequence measurement devices of Comparative examples 1 to 3.

After that, the solid phase surface was washed to remove unfixed excess probes, and thereby a nucleic acid sequence measurement device 1 consisting of the fluorescent probe 1 and the quenching probe 1 was produced (FIG. 8).

Table 1 shows the lengths of the fluorescent probe and the quenching probe of the nucleic acid sequence measurement device 1 and the portion of the quenching probe to which the fluorescent probe bound.

Figure 9:
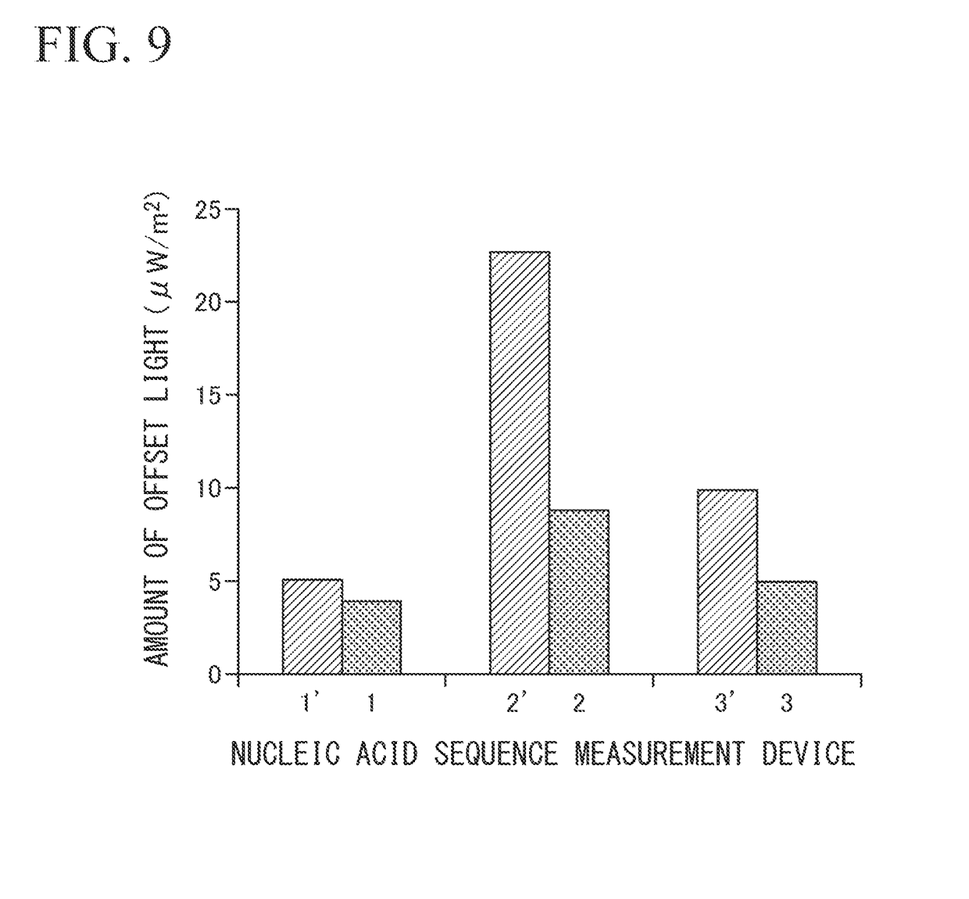
FIG. 9 is a graph in which the amounts of offset light of the nucleic acid sequence measurement devices of Examples 1 to 3 are compared with the amounts of offset light of the nucleic acid measurement devices of Comparative examples 1 to 3.

Next, the amount of offset light of the nucleic acid sequence measurement device 1 produced as described above was measured. The result is shown in FIG. 9.

Example 2

A nucleic acid sequence measurement device 2 consisting of a fluorescent probe 2 and a quenching probe 1 was produced (FIG. 8) similarly to Example 1, except for using, instead of the fluorescent probe 1, the fluorescent probe 2 which had a binding position of a fluorescent molecule of the fluorescent probe 1 set to the base end on the side opposite to the base end of the fluorescent probe on the solid phase surface side.

Table 1 shows the lengths of the fluorescent probe and the quenching probe of the nucleic acid sequence measurement device 2 and the portion of the quenching probes to which the fluorescent probe bound.

Next, the amount of offset light of the nucleic acid sequence measurement device 2 produced as described above was measured. The result is shown in FIG. 9.

Example 3

A nucleic acid sequence measurement device 3 consisting of a fluorescent probe 3 and a quenching probe 3 was produced (FIG. 8) except for using, instead of the fluorescent probe 1, the fluorescent probe 3 having a length 34 of the detection sequence of the fluorescent probe 1 and using, instead of the quenching probe 1, the quenching probe 3 having a complementary nucleic acid sequence to the portion of 24 bases from the base end of the detection sequence of the fluorescent probe 3 on the solid phase surface side and a quenching molecule binding to the base end on the side opposite to the base end on the solid phase surface side. Further, a fluorescent molecule of the fluorescent probe 3 bound to the fluorescent probe 3 at the position of the same height as the height of the quenching molecule of the quenching probe 3 from the solid phase surface.

Table 1 shows the lengths of the fluorescent probe and the quenching probe of the nucleic acid sequence measurement device 3 and the portion of the quenching probe to which the fluorescent probe bound.

Next, the amount of offset light of the nucleic acid sequence measurement device 3 produced as described above was measured. The result is shown in FIG. 9.

Comparative Example 1

A nucleic acid sequence measurement device 1' consisting of a fluorescent probe 1' and a quenching probe 1' was produced (FIG. 8) similarly to Example 1, except for using, instead of the fluorescent probe 1, the fluorescent probe 1' having a linker sequence, a detection sequence having a length 28 of a nucleic acid sequence, and a fluorescent molecule binding to the base end on the side opposite to the base end on the solid phase surface side and using, instead of the quenching probe 1, the quenching probe 1' having a linker sequence, a nucleic acid sequence having a length 28 and being complementary to a part of a nucleic acid sequence on the base end side on the side opposite to the base end of the detection sequence of the fluorescent probe 1' on the solid phase surface side (which will also be referred to as a tip end sequence), and a quenching molecule binding to the base end on the side opposite to the base end on the solid phase surface side.

Table 1 shows the lengths of the fluorescent probe and the quenching probe of the nucleic acid sequence measurement device 1' and the portion of the quenching probe to which the fluorescent probe bound.

Next, the amount of offset light of the nucleic acid sequence measurement device 1' produced as described above was measured. The result is shown in FIG. 9.

Comparative Example 2

A nucleic acid sequence measurement device 2' consisting of a fluorescent probe 2' and a quenching probe 2' was produced (FIG. 8) similarly to Example 1, except for using, instead of the fluorescent probe 1, the fluorescent probe 2' having a linker sequence, a detection sequence having a length 33 of a nucleic acid sequence, and a fluorescent molecule binding to the base end on the side opposite to the base end on the solid phase surface side, and using, instead of the quenching probe 1, the quenching probe 2' having a linker sequence, a nucleic acid sequence having a length 28 with a part of a tip end sequence being complementary to the fluorescent probe 2', and a quenching molecule binding to the base end on the side opposite to the base end on the solid phase surface side.

Table 1 shows the lengths of the fluorescent probe and the quenching probe of the nucleic acid sequence measurement device 2' and the portion of the quenching probe to which the fluorescent probe bound.

Next, the amount of offset light of the nucleic acid sequence measurement device 2' produced as described above was measured. The result is shown in FIG. 9.

Comparative Example 3

A nucleic acid sequence measurement device 3' consisting of a fluorescent probe 3' and a quenching probe 3' was produced (FIG. 8) similarly to Example 1, except for using, instead of the fluorescent probe 1, the fluorescent probe 3' having a linker sequence, a detection sequence having a length 24 of a nucleic acid sequence, and a fluorescent molecule binding to the base end on the side opposite to the base end on the solid phase surface side, and using, instead of the quenching probe 1, the quenching probe 3' having a linker sequence, a nucleic acid sequence having a length 24 and being complementary to a part of a tip end sequence of the fluorescent probe 3', and a quenching molecule binding to the base end on the side opposite to the base end on the solid phase surface side.

Table 1 shows the lengths of the fluorescent probe and the quenching probe of the nucleic acid sequence measurement device 3' and the portion of the quenching probe to which the fluorescent probe bound.

Next, the amount of offset light of the nucleic acid sequence measurement device 3' produced as described above was measured. The result is shown in FIG. 9.

TABLE 1

| | Nucleic acid sequence measurement device | Probe | Probe length | Binding sequence |
|---|---|---|---|---|
| Example 1 | 1 | Fluorescent probe 1 | 33 | Entire sequence of quenching probe excluding linker sequence |
| | | Quenching probe 1 | 28 | |
| Example 2 | 2 | Fluorescent probe 2 | 33 | Entire sequence of quenching probe excluding linker sequence |
| | | Quenching probe 1 | 28 | |
| Example 3 | 3 | Fluorescent probe 3 | 34 | Entire sequence of quenching probe excluding linker sequence |
| | | Quenching probe 3 | 24 | |
| Comparative example 1 | 1' | Fluorescent probe 1' | 28 | Part of tip end sequence |
| | | Quenching probe 1' | 28 | |
| Comparative example 2 | 2' | Fluorescent probe 2' | 33 | Part of tip end sequence |
| | | Quenching probe 2' | 28 | |
| Comparative example 3 | 3' | Fluorescent probe 3' | 24 | Part of tip end sequence |
| | | Quenching probe 3' | 24 | |

The nucleic acid sequence measurement devices of Examples 1 to 3 in which the fluorescent probes bound to the quenching probes at the entire nucleic acid sequence portion of the quenching probes excluding the linker sequences had a reduced amount of offset light compared to the nucleic acid sequence measurement devices of Comparative examples 1 to 3 in which the fluorescent probes bound to the quenching probes in the portions of the tip end sequences of the quenching probes as shown in FIG. 9. As a result, it has been found that the nucleic acid sequence measurement devices of Examples 1 to 3 can reduce the minimum amount of light which can be detected and the detection sensitivity thereof can be improved.

In addition, although the amount of offset light was smaller when the fluorescent molecule was positioned close to the quenching molecule than when the fluorescent molecule was positioned to be separate from the quenching molecule in all of Examples 1 to 3 and Comparative examples 1 to 3, the nucleic acid sequence measurement device of Example 2 in which the fluorescent molecule was positioned to be separate from the quenching molecule had a smaller amount of offset light than the nucleic acid sequence measurement device of Comparative example 2 in which the fluorescent molecule was likewise positioned to be separate from the quenching molecule.

Although exemplary examples of the present invention have been described above, the present invention is not limited thereto. Addition, omission, substitution, and other modification of the configuration can be made within the scope not departing from the gist of the present invention. The present invention is not limited by the above description, and limited only by the range of the accompanying claims.

REFERENCE SIGNS LIST

10 Fluorescent probe
11 Fluorescent molecule
12 Complementary sequence
13 Detection sequence
14 Linker
20 Quenching probe
21 Quenching molecule
22 Complementary sequence
23 Detection sequence
24 Linker
60 Fluorescence reader
100 Solid phase surface

The invention claimed is:

1. A nucleic acid sequence measurement device that measures a target having a specific nucleic acid sequence by means of hybridization, a sample being a solution containing the target, the nucleic acid sequence measurement device comprising:
   a fluorescent probe with a fluorescent molecule added at a predetermined position;
   a quenching probe with a quenching molecule added at a predetermined position; and
   a substrate having a solid phase surface to which a base end of each of the fluorescent probe and the quenching probe is fixed,
   wherein one of the fluorescent probe and the quenching probe has a detection sequence having a nucleic acid sequence complementary to a nucleic acid sequence of the target,
   wherein the other one of the fluorescent probe and the quenching probe has a nucleic acid sequence complementary to a nucleic acid sequence of a part of the detection sequence (which will also be referred to as a complementary sequence) and a nucleic acid sequence from a base end of the complementary sequence on a side of the solid phase surface to the other base end is complementary to the part of the detection sequence,
   wherein the fluorescent probe or the quenching probe having the detection sequence has a longer nucleic acid sequence than the fluorescent probe or the quenching probe having the complementary sequence,
   wherein the base end of the fluorescent probe and the base end of the quenching probe are fixed to the solid phase surface so that a positional relationship in which fluorescence emitted by the fluorescent molecule is quenched by the quenching molecule close to the fluorescent molecule is established, and wherein the nucleic acid sequence from the base end of the complementary sequence on the side of the solid phase surface to the other base end is complementary to a nucleic acid sequence from a base end of the detection sequence on the side of the solid phase surface to a portion corresponding to the other base end of the complementary sequence.

2. The nucleic acid sequence measurement device according to claim 1, wherein
in a case where hybridization of the target and the detection sequence does not occur, binding of the fluorescent probe and the quenching probe is maintained, which causes fluorescence emitted by the fluorescent molecule to be quenched by the quenching molecule close to the fluorescent molecule, and
in a case where hybridization of the target and the detection sequence occurs, binding of the fluorescent probe and the quenching probe is released, which causes the fluorescent molecule to separate from the quenching molecule and emit fluorescence.

3. The nucleic acid sequence measurement device according to claim 1, wherein the quenching probe has the detection sequence.

4. The nucleic acid sequence measurement device according to claim 1, wherein the substrate is a flat plate, and the solid phase surface is one plane of the flat plate.

5. The nucleic acid sequence measurement device according to claim 1, wherein the substrate is a bead, and the solid phase surface is a surface of the bead.

6. The nucleic acid sequence measurement device according to claim 1, wherein a number of quenching probes is greater than a number of fluorescent probes.

7. The nucleic acid sequence measurement device according to claim 1, wherein a number of fluorescent probes is greater than a number of quenching probes.

8. The nucleic acid sequence measurement device according to claim 1, wherein a number of quenching molecules is greater than a number of fluorescent molecules.

9. The nucleic acid sequence measurement device according to claim 8, wherein a ratio of the number of fluorescent molecules to the number of quenching molecules is 2:3.

10. The nucleic acid sequence measurement device according to claim 1, wherein the predetermined position at which the fluorescent molecule is added is in the middle of the fluorescent probe.

11. The nucleic acid sequence measurement device according to claim 1, wherein the predetermined position at which the quenching molecule is added is in the middle of the quenching probe.

12. The nucleic acid sequence measurement device according to claim 1, wherein a number of predetermined positions at which the fluorescent molecule is added is multiple.

13. The nucleic acid sequence measurement device according to claim 1, wherein a number of predetermined positions at which the quenching molecule is added is multiple.

14. The nucleic acid sequence measurement device according to claim 12, wherein multiple fluorescent molecules of different types are added at the predetermined positions.

15. The nucleic acid sequence measurement device according to claim 13, wherein multiple quenching molecules of different types are added at the predetermined positions.

* * * * *